(12) United States Patent
Oikawa

(10) Patent No.: US 11,904,275 B2
(45) Date of Patent: Feb. 20, 2024

(54) CARBON DIOXIDE TREATMENT APPARATUS, CARBON DIOXIDE TREATMENT METHOD, AND METHOD OF PRODUCING CARBON COMPOUND

(71) Applicant: HONDA MOTOR CO., LTD., Tokyo (JP)

(72) Inventor: Hiroshi Oikawa, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 17/674,935

(22) Filed: Feb. 18, 2022

(65) Prior Publication Data

US 2022/0274061 A1    Sep. 1, 2022

(30) Foreign Application Priority Data

Feb. 26, 2021    (JP) .................................. 2021-030950

(51) Int. Cl.
*B01D 53/62* (2006.01)
*B01D 53/96* (2006.01)
(Continued)

(52) U.S. Cl.
CPC .......... *B01D 53/965* (2013.01); *B01D 53/62* (2013.01); *B01D 53/78* (2013.01); *C07C 2/08* (2013.01);
(Continued)

(58) Field of Classification Search
None
See application file for complete search history.

(56) References Cited

U.S. PATENT DOCUMENTS

| 4,197,421 A * | 4/1980 | Steinberg ................. C10G 3/49 |
| | | 205/555 |
| 2004/0166412 A1 | 8/2004 | Bugnet et al. |

(Continued)

FOREIGN PATENT DOCUMENTS

| JP | 2001-035526 | 2/2001 |
| JP | 2004-538609 | 12/2004 |

(Continued)

OTHER PUBLICATIONS

Japanese Office Action for Japanese Patent Application No. 2021-030950 dated Apr. 4, 2023.

(Continued)

*Primary Examiner* — Tam M Nguyen
(74) *Attorney, Agent, or Firm* — Amin, Turocy & Watson, LLP

(57) ABSTRACT

An object of the present invention is to provide a carbon dioxide treatment apparatus, a carbon dioxide treatment method, and a method of producing carbon compounds, which have high energy efficiency from carbon dioxide capture to reduction and a high carbon dioxide loss reduction effect. In a carbon dioxide treatment apparatus 100 including: a capturing device 1 that captures carbon dioxide; and an electrochemical reaction device 2 that electrochemically reduces carbon dioxide, an absorption unit 12 of the capturing device 1 brings an electrolytic solution A composed of a strong alkaline aqueous solution and carbon dioxide gas into contact with each other to dissolve carbon dioxide in the electrolytic solution A and absorb the carbon dioxide, supplies an electrolytic solution B that has absorbed carbon dioxide between the cathode and the anode of the electrochemical reaction device 2, and electrochemically reduces the dissolved carbon dioxide in the electrolytic solution at the cathode.

6 Claims, 6 Drawing Sheets

(51) Int. Cl.
  *B01D 53/78* (2006.01)
  *C25B 1/04* (2021.01)
  *C25B 3/03* (2021.01)
  *C25B 3/07* (2021.01)
  *C25B 3/26* (2021.01)
  *C25B 9/65* (2021.01)
  *C25B 9/17* (2021.01)
  *C25B 15/08* (2006.01)
  *H01M 8/18* (2006.01)
  *C07C 2/08* (2006.01)

(52) U.S. Cl.
  CPC ............... *C25B 1/04* (2013.01); *C25B 3/03* (2021.01); *C25B 3/07* (2021.01); *C25B 3/26* (2021.01); *C25B 9/17* (2021.01); *C25B 9/65* (2021.01); *C25B 15/081* (2021.01); *C25B 15/085* (2021.01); *C25B 15/087* (2021.01); *H01M 8/186* (2013.01); *B01D 2251/306* (2013.01); *B01D 2251/604* (2013.01); *B01D 2257/504* (2013.01); *B01D 2258/06* (2013.01); *H01M 2300/0014* (2013.01)

(56) References Cited

U.S. PATENT DOCUMENTS

| | | | | |
|---|---|---|---|---|
| 2014/0151240 | A1* | 6/2014 | Bedell | B01D 53/1475 205/462 |
| 2018/0264429 | A1 | 9/2018 | Sugano et al. | |
| 2018/0274108 | A1 | 9/2018 | Ono et al. | |
| 2019/0233952 | A1 | 8/2019 | Sheehan | |
| 2022/0118406 | A1* | 4/2022 | Lackner | C25B 9/19 |
| 2022/0282384 | A1* | 9/2022 | Shimada | C25B 15/08 |
| 2022/0282387 | A1* | 9/2022 | Shimada | C25B 15/08 |
| 2022/0307145 | A1* | 9/2022 | Shimada | C25B 9/19 |
| 2023/0119993 | A1* | 4/2023 | Oikawa | C25B 9/15 205/462 |

FOREIGN PATENT DOCUMENTS

| | | |
|---|---|---|
| JP | 2018-154898 | 10/2018 |
| JP | 2019-167556 | 10/2019 |
| JP | 2019-183286 | 10/2019 |
| JP | 2020-087554 | 6/2020 |
| JP | 2020-147776 | 9/2020 |
| WO | 2018/232515 | 12/2018 |
| WO | 2020/109295 | 6/2020 |

OTHER PUBLICATIONS

Japanese Office Action for Japanese Patent Application No. 2021-030950 dated Oct. 4, 2022.

Chinese Office Action for Chinese Patent Application No. 202210168655.4 dated Jul. 11, 2023.

* cited by examiner

CARBON DIOXIDE TREATMENT APPARATUS, CARBON DIOXIDE TREATMENT METHOD, AND METHOD OF PRODUCING CARBON COMPOUND

BACKGROUND OF THE INVENTION

Field of the Invention

The present invention relates to a carbon dioxide treatment apparatus, a carbon dioxide treatment method, and a method of producing carbon compounds.

Description of Related Art

Technology to capture exhaust gases and carbon dioxide in the atmosphere and obtain valuable resources by electrochemical reduction is promising in that it has a possibility of achieving carbon neutrality, but the economic efficiency thereof is its biggest issue. In order to improve economic efficiency in carbon dioxide capture and reduction, it is important to improve energy efficiency and reduce carbon dioxide loss.

As a technology for capturing carbon dioxide, one is known in which carbon dioxide in a gas is physically or chemically adsorbed on a solid or liquid adsorbent and then desorbed by energy such as heat. In addition, regarding a technology for electrochemically reducing carbon dioxide, one using a cathode having a catalyst layer formed using a carbon dioxide reduction catalyst on the side of a gas diffusion layer in contact with an electrolytic solution and in which carbon dioxide is supplied from a side opposite to the catalyst layer on the gas diffusion layer and electrochemically reduced is used (for example, Patent Document 1).

PATENT DOCUMENTS

[Patent Document 1] PCT International Publication No. 2018/232515

SUMMARY OF THE INVENTION

However, in the related art, the technology for capturing carbon dioxide and the technology for electrochemically reducing carbon dioxide have been researched and developed separately. Therefore, although the overall energy efficiency and carbon dioxide loss reduction effect in a case where each technology is combined can be determined in a multiplier manner from the efficiency of each technology, there is room for further improvement. In this manner, it can be said that it is important to improve the energy efficiency and carbon dioxide loss reduction effect from a comprehensive point of view when combining the technology of capturing carbon dioxide and the technology of electrochemically reducing carbon dioxide.

An object of the present invention is to provide a carbon dioxide treatment apparatus, a carbon dioxide treatment method, and a method of producing a carbon compounds, which have high energy efficiency of carbon dioxide capture and reduction and a high carbon dioxide loss reduction effect.

The present invention has adopted the following aspects.

(1) According to an aspect of the present invention, a carbon dioxide treatment apparatus (for example, a carbon dioxide treatment apparatus 100 of an embodiment) is provided including: a capturing device (for example, a capturing device 1 of the embodiment) that captures carbon dioxide; and an electrochemical reaction device (for example, an electrochemical reaction device 2 of the embodiment) that electrochemically reduces carbon dioxide, in which the capturing device includes an absorption unit (for example, an absorption unit 12 of the embodiment) that brings an electrolytic solution composed of a strong alkaline aqueous solution and carbon dioxide gas into contact with each other to dissolve carbon dioxide in the electrolytic solution and absorb the carbon dioxide, and the electrochemical reaction device includes a cathode (for example, a cathode 21 of the embodiment), an anode (for example, an anode 22 of the embodiment), and a liquid flow path (for example, a liquid flow path 23a of the embodiment) provided between the cathode and the anode through which the electrolytic solution that has absorbed carbon dioxide in the absorption unit flows, and reduces the dissolved carbon dioxide in the electrolytic solution at the cathode.

(2) In the carbon dioxide treatment apparatus according to an aspect of the present invention, a power storage device (for example, a power storage device 3 of the embodiment) that supplies power to the electrochemical reaction device may be additionally provided, and the power storage device may include a conversion unit (for example, a conversion unit 31 of the embodiment) that converts renewable energy into electric energy, and a storage unit (for example, a storage unit 32 of the embodiment) that stores the electric energy converted by the conversion unit.

(3) The storage unit may be a nickel-hydride battery, the nickel-hydride battery may have a positive electrode (for example, a positive electrode 33 of the embodiment), a negative electrode (for example, a negative electrode 34 of the embodiment), a separator (for example, a separator 35 of the embodiment) provided between the positive electrode and the negative electrode, a positive electrode side flow path (for example, a positive electrode side flow path 36 of the embodiment) provided between the positive electrode and the separator, and a negative electrode side flow path (for example, a negative electrode side flow path 37 of the embodiment) provided between the negative electrode and the separator, when the nickel-hydride battery is discharged, the electrolytic solution may be circulated in the order of the absorption unit, the positive electrode side flow path, the electrochemical reaction device, the negative electrode side flow path, and the absorption unit, and when the nickel-hydride battery is charged, the electrolytic solution may be circulated in the order of the absorption unit, the negative electrode side flow path, the electrochemical reaction device, the positive electrode side flow path, and the absorption unit.

(4) The capturing device may further have a concentration unit (for example, concentration units 11 and 13 of the embodiment) that concentrates carbon dioxide, and carbon dioxide gas may be supplied from the concentration unit to a side of the cathode opposite to the anode.

(5) The carbon dioxide treatment apparatus according to an aspect of the present invention may further include a homologation reaction device (for example, a homologation reaction device 4 of the embodiment) that increases the number of carbons by multimerizing ethylene generated by reducing carbon dioxide in the electrochemical reaction device.

(6) The carbon dioxide treatment apparatus according to an aspect of the present invention may further include a heat exchanger (for example, a heat exchanger 5 of the embodiment) that heats the electrolytic solution by exchanging heat between a heat medium heated by the heat generated by reaction in the homologation reaction device and the electrolytic solution.

(7) The carbon dioxide treatment apparatus according to an aspect of the present invention may further include an ethanol purification device (for example, an ethanol purification device 6 of the embodiment) that purifies ethanol generated by reducing carbon dioxide by the electrochemical reaction device.

(8) According to another aspect of the present invention, a carbon dioxide treatment method is provided including: a step of bringing carbon dioxide gas into contact with an electrolytic solution composed of a strong alkaline aqueous solution to dissolve carbon dioxide in the electrolytic solution and absorb the carbon dioxide; and a step of supplying the electrolytic solution between the cathode and the anode and electrochemically reducing dissolved carbon dioxide in the electrolytic solution to generate carbon compounds and hydrogen.

(9) The carbon dioxide gas may be supplied to the side of the cathode opposite to the anode, and the carbon dioxide gas may be electrochemically reduced together with the dissolved carbon dioxide.

(10) According to another aspect of the present invention, a method of producing carbon compounds is provided in which carbon dioxide is reduced by using the carbon dioxide treatment method according to (8) or (9).

(11) The method of producing carbon compounds according to an aspect of the present invention may further include a step of multimerizing ethylene generated by reducing the dissolved carbon dioxide.

(12) The method of producing carbon compounds according to an aspect of the present invention may further include a step of purifying ethanol generated by reducing the dissolved carbon dioxide.

According to the aspects (1) to (12), it is possible to provide a carbon dioxide treatment apparatus, a carbon dioxide treatment method, and a method of producing carbon compounds, which have energy efficiency of carbon dioxide capture and reduction and a high carbon dioxide loss reduction effect.

DETAILED DESCRIPTION OF THE INVENTION

Figure 1:
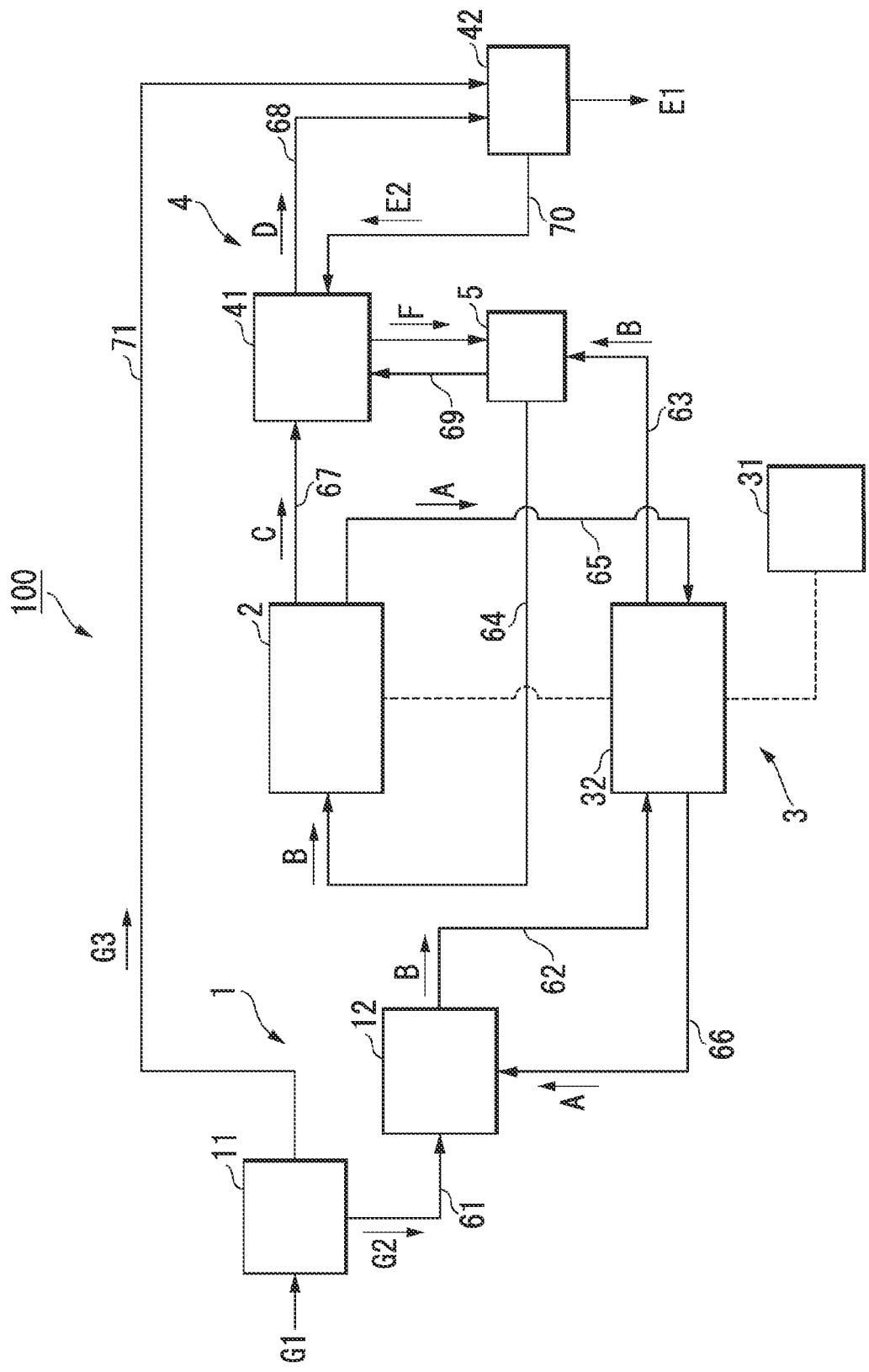
FIG. 1 is a block diagram illustrating a carbon dioxide treatment apparatus according to an embodiment.

Hereinafter, embodiments of the present invention will be described with reference to the drawings. In addition, the dimensions and the like in the drawings exemplified in the following description are examples, and the present invention is not necessarily limited thereto, and the present invention can be appropriately changed without changing the gist thereof.

[Carbon Dioxide Treatment Apparatus]

As illustrated in FIG. 1, a carbon dioxide treatment apparatus 100 according to an aspect of the present invention includes a capturing device 1, an electrochemical reaction device 2, a power storage device 3, a homologation reaction device 4, and a heat exchanger 5. The capturing device 1 includes a concentration unit 11 and an absorption unit 12. The power storage device 3 includes a conversion unit 31 and a storage unit 32 electrically connected to the conversion unit 31. The homologation reaction device 4 includes a reactor 41 and a gas-liquid separator 42.

In the carbon dioxide treatment apparatus 100, the concentration unit 11 and the absorption unit 12 are connected by a gas flow path 61. The absorption unit 12 and the storage unit 32 are connected by a liquid flow path 62 and a liquid flow path 66. The storage unit 32 and the heat exchanger 5 are connected by a liquid flow path 63. The heat exchanger 5 and the electrochemical reaction device 2 are connected by a liquid flow path 64. The electrochemical reaction device 2 and the storage unit 32 are connected by a liquid flow path 65. The electrochemical reaction device 2 and the reactor 41 are connected by a gas flow path 67. The reactor 41 and the gas-liquid separator 42 are connected by a gas flow path 68 and a gas flow path 70. A circulation flow path 69 of heat medium is provided between the reactor 41 and the heat exchanger 5. The concentration unit 11 and the gas-liquid separator 42 are connected by a gas flow path 71.

Each of these flow paths is not particularly limited, and known piping or the like can be appropriately used therefor. Air feeding means such as a compressor, a pressure reducing valve, measuring equipment such as a pressure gauge, and the like can be appropriately installed in the gas flow paths 61, 67, 68, 70, and 71. Further, liquid feeding means such as a pump, measuring equipment such as a flowmeter, and the like can be appropriately installed in the liquid flow paths 62 to 66.

The capturing device 1 is a device that captures carbon dioxide.

Gas G1 containing carbon dioxide such as the atmosphere and exhaust gas is supplied to the concentration unit 11. In the concentration unit 11, carbon dioxide of the gas G1 is concentrated. As the concentration unit 11, a known concentrating device can be adopted as long as the device can concentrate carbon dioxide. For example, a membrane separation device utilizing differences in permeation speed with respect to the membrane, or an adsorption/separation device utilizing chemical or physical adsorption or desorption can be used. Among these, adsorption using temperature swing adsorption is particularly preferable from the viewpoint of exceptional separation performance.

Concentrated gas G2 in which carbon dioxide has been concentrated in the concentration unit 11 is fed to the absorption unit 12 through the gas flow path 61. Further, separated gas G3 separated from the concentrated gas G2 is fed to the gas-liquid separator 42 through the gas flow path 71.

In the absorption unit 12, the carbon dioxide gas in the concentrated gas G2 supplied from the concentration unit 11 comes into contact with an electrolytic solution A, and the carbon dioxide dissolves in the electrolytic solution A and absorbed. The method of bringing the carbon dioxide gas and the electrolytic solution A into contact with each other is not particularly limited, and examples thereof include a method of blowing the concentrated gas G2 into the electrolytic solution A and bubbling.

In the absorption unit 12, the electrolytic solution A composed of a strong alkaline aqueous solution is used as an absorption solution for absorbing carbon dioxide. In carbon dioxide, the carbon atom is positively charged (δ+) because the oxygen atom strongly attracts electrons. Therefore, in a strong alkaline aqueous solution in which a large amount of hydroxide ions are present, the dissolution reaction of carbon dioxide easily proceeds from the hydrated state to $CO_3^{2-}$ via $HCO^{3-}$, and the equilibrium state in which the abundance of $CO_3^{2-}$ is high is obtained. Based on this, carbon dioxide dissolves more readily in a strong alkaline aqueous solution than other gases such as nitrogen, hydrogen, and oxygen, and carbon dioxide in the concentrated gas G2 is selectively absorbed to the electrolytic solution A by the absorption unit 12. In this manner, the concentration of carbon dioxide can be assisted by using the electrolytic solution A in the absorption unit 12. Therefore, it is not necessary to concentrate carbon dioxide to a high concentration in the concentration unit 11, and the energy required for concentration in the concentration unit 11 can be reduced.

An electrolytic solution B in which carbon dioxide has been absorbed by the absorption unit 12 is fed to the electrochemical reaction device 2 through the liquid flow path 62, the storage unit 32, the liquid flow path 63, the heat exchanger 5, and the liquid flow path 64. Further, the electrolytic solution A flowing out of the electrochemical reaction device 2 is fed to the absorption unit 12 through the liquid flow path 65, the storage unit 32, and the liquid flow path 66. In this manner, in the carbon dioxide treatment apparatus 100, the electrolytic solution is circulated and shared between the absorption unit 12, the storage unit 32, and the electrochemical reaction device 2.

Examples of the strong alkaline aqueous solution used for the electrolytic solution A include a potassium hydroxide aqueous solution and a sodium hydroxide aqueous solution. Among these, a potassium hydroxide aqueous solution is preferable from the viewpoint that carbon dioxide has exceptional solubility in a potassium hydroxide aqueous solution in the absorption unit 12 and in this case the reduction of carbon dioxide in the electrochemical reaction device 2 is promoted.

Figure 2:
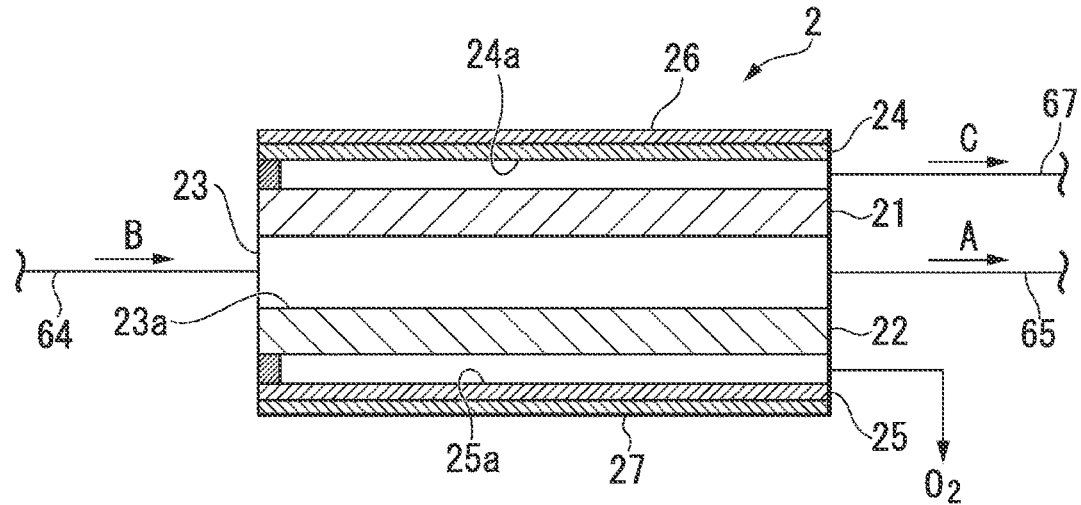
FIG. 2 is a schematic sectional view illustrating an example of an electrolytic cell of an electrochemical reaction device.

The electrochemical reaction device 2 is a device that electrochemically reduces carbon dioxide. As illustrated in FIG. 2, the electrochemical reaction device 2 includes a cathode 21, an anode 22, a liquid flow path structure 23 for forming the liquid flow path 23a, a gas flow path structure 24 in which a gas flow path 24a is formed, a gas flow path structure 25 in which a gas flow path 25a is formed, a power supplying body 26, and a power supplying body 27.

In the electrochemical reaction device 2, the power supplying body 26, the gas flow path structure 24, the cathode 21, the liquid flow path structure 23, the anode 22, the gas flow path structure 25, and the power supplying body 27 are laminated in this order. A slit is formed in the liquid flow path structure 23, and the region surrounded by the cathode 21, the anode 22, and the liquid flow path structure 23 in the slit is the liquid flow path 23a. A groove is formed on the cathode 21 side of the gas flow path structure 24, and part of the groove surrounded by the gas flow path structure 24 and the cathode 21 is the gas flow path 24a. A groove is formed on the anode 22 side of the gas flow path structure 25, and part of the groove surrounded by the gas flow path structure 25 and the anode 22 is the gas flow path 25a.

In this manner, in the electrochemical reaction device 2, the liquid flow path 23a is formed between the cathode 21 and the anode 22, the gas flow path 24a is formed between the cathode 21 and the power supplying body 26, and the gas flow path 25a is formed between the anode 22 and the power supplying body 27. The power supplying body 26 and the power supplying body 27 are electrically connected to the storage unit 32 of the power storage device 3. Further, the gas flow path structure 24 and the gas flow path structure 25 are conductors, and a voltage can be applied between the cathode 21 and the anode 22 by the power supplied from the storage unit 32.

The cathode 21 is an electrode that reduces carbon dioxide to generate carbon compounds and reduces water to generate hydrogen. The cathode 21 may be any electrode as long as the electrode can electrochemically reduce carbon dioxide and the generated gaseous carbon compounds and hydrogen permeate therethrough to the gas flow path 24a. Examples thereof include an electrode in which a cathode catalyst layer is formed on the liquid flow path 23a side of a gas diffusion layer. A part of the cathode catalyst layer may enter the gas diffusion layer. A porous layer that is denser than the gas diffusion layer may be disposed between the gas diffusion layer and the cathode catalyst layer.

As the cathode catalyst that forms the cathode catalyst layer, a known catalyst that promotes the reduction of carbon dioxide can be used. Specific examples of the cathode catalyst include metals such as gold, silver, copper, platinum, palladium, nickel, cobalt, iron, manganese, titanium, cadmium, zinc, indium, gallium, lead, and tin; alloys and intermetallic compounds of these metals; and metal complexes such as a ruthenium complex and a rhenium complex. Among these, copper and silver are preferable, and copper is more preferable, from the viewpoint that the reduction of carbon dioxide is promoted therewith. As the cathode catalyst, one type may be used alone, or two or more types may be used in combination.

As the cathode catalyst, a supported catalyst in which metal particles are supported on a carbon material (carbon particles, carbon nanotubes, graphene, and the like) may be used.

The gas diffusion layer of the cathode 21 is not particularly limited, and examples thereof include carbon paper and carbon cloth.

The method of producing the cathode 21 is not particularly limited, and examples thereof include a method of applying a liquid composition containing a cathode catalyst to a surface of the gas diffusion layer on the liquid flow path 23a side and drying the liquid composition.

The anode 22 is an electrode for oxidizing hydroxide ions to generate oxygen. The anode 22 may be any electrode as long as the electrode can electrochemically oxidize hydroxide ions and the generated oxygen permeates therethrough to the gas flow path 25a. Examples thereof include an electrode in which an anode catalyst layer is formed on the liquid flow path 23a side of the gas diffusion layer.

The anode catalyst that forms the anode catalyst layer is not particularly limited, and a known anode catalyst can be used. Specifically, examples thereof include metals such as platinum, palladium and nickel; alloys and intermetallic compounds of these metals; metal oxides such as manganese oxide, iridium oxide, nickel oxide, cobalt oxide, iron oxide, tin oxide, indium oxide, ruthenium oxide, lithium oxide, and lanthanum oxide; and metal complexes such as a ruthenium complex and a rhenium complex. As the anode catalyst, one type may be used alone, or two or more types may be used in combination.

Examples of the gas diffusion layer of the anode 22 include carbon paper and carbon cloth. Further, as the gas diffusion layer, a porous body such as a mesh material, a punching material, a porous material, or a metal fiber sintered body may be used. Examples of the material of the porous body include metals such as titanium, nickel, and iron, and alloys (for example, SUS) of these metals.

Examples of the material of the liquid flow path structure 23 include a fluorocarbon resin such as polytetrafluoroethylene.

Examples of the materials of the gas flow path structures 24 and 25 include metals such as titanium and SUS; and carbon.

Examples of the material of the power supplying bodies 26 and 27 include metals such as copper, gold, titanium, and SUS; and carbon. For the power supplying bodies 26 and 27, those having a surface of a copper base material plated with gold or the like may be used.

The electrochemical reaction device 2 is a flow cell in which the electrolytic solution B supplied from the absorption unit 12 flows through the liquid flow path 23a. Then, when a voltage is applied to the cathode 21 and the anode 22, the dissolved carbon dioxide in the electrolytic solution B flowing through the liquid flow path 23a is electrochemically reduced at the cathode 21 to generate carbon compounds and hydrogen. Since carbon dioxide dissolves in the electrolytic solution B at the inlet of the liquid flow path 23a, the electrolytic solution B is in a weak alkaline state in which the abundance of $CO_3^{2-}$ is high as described above. On the other hand, as the reduction proceeds, the amount of dissolved carbon dioxide decreases, and the electrolytic solution A in a strong alkaline state is obtained at the outlet of the liquid flow path 23a.

Examples of the carbon compounds generated by reducing carbon dioxide at the cathode 21 include carbon monoxide, ethylene, and ethanol. For example, the following reaction generates carbon monoxide and ethylene as gaseous products. Hydrogen is also generated at the cathode 21 by the following reaction. The generated gaseous carbon compounds and hydrogen permeate through the gas diffusion layer of the cathode 21 and flow out of the gas flow path 24a.

$$CO_2+H_2O \rightarrow CO+2OH^-$$

$$2CO+8H_2O \rightarrow C_2H_4+8OH^-+2H_2O$$

$$2H_2O \rightarrow H_2+2OH^-$$

Further, the hydroxide ions generated at the cathode 21 move in the electrolytic solution B to the anode 22 and are oxidized by the following reaction to generate oxygen. The generated oxygen permeates through the gas diffusion layer of the anode 22 and is discharged from the gas flow path 25a.

$$4OH^- \rightarrow O^2+2H_2O$$

In this manner, in the carbon dioxide treatment apparatus 100, the electrolytic solution used for the electrochemical reaction device 2 is shared for the absorption solution of the absorption unit 12, and carbon dioxide is supplied to the electrochemical reaction device 2 while dissolving in the electrolytic solution B and is electrochemically reduced. Accordingly, for example, compared to a case where carbon dioxide is adsorbed on an adsorbent and desorbed by heating for reduction, the energy required for desorption of carbon dioxide is reduced, energy efficiency can be improved, and carbon dioxide loss can be also reduced.

The power storage device 3 is a device that supplies power to the electrochemical reaction device 2.

In the conversion unit 31, renewable energy is converted into electric energy. The conversion unit 31 is not particularly limited, and examples thereof include a wind power generator, a solar power generator, and a geothermal power generator. The number of conversion units 31 included in the power storage device 3 may be one, or may be two or more.

The electric energy converted by the conversion unit 31 is stored in the storage unit 32. By storing the converted electric energy in the storage unit 32, it is possible to stably supply power to the electrochemical reaction device 2 even during a time period when the conversion unit is not generating power. Further, in a case where renewable energy is used, voltage fluctuations tend to be large in general, but once stored in the storage unit 32, power can be supplied to the electrochemical reaction device 2 at a stable voltage.

The storage unit 32 in this example is a nickel-hydride battery. In addition, the storage unit 32 may be any battery as long as the battery can be charged and discharged, and may be, for example, a lithium-ion secondary battery or the like.

Figure 3:
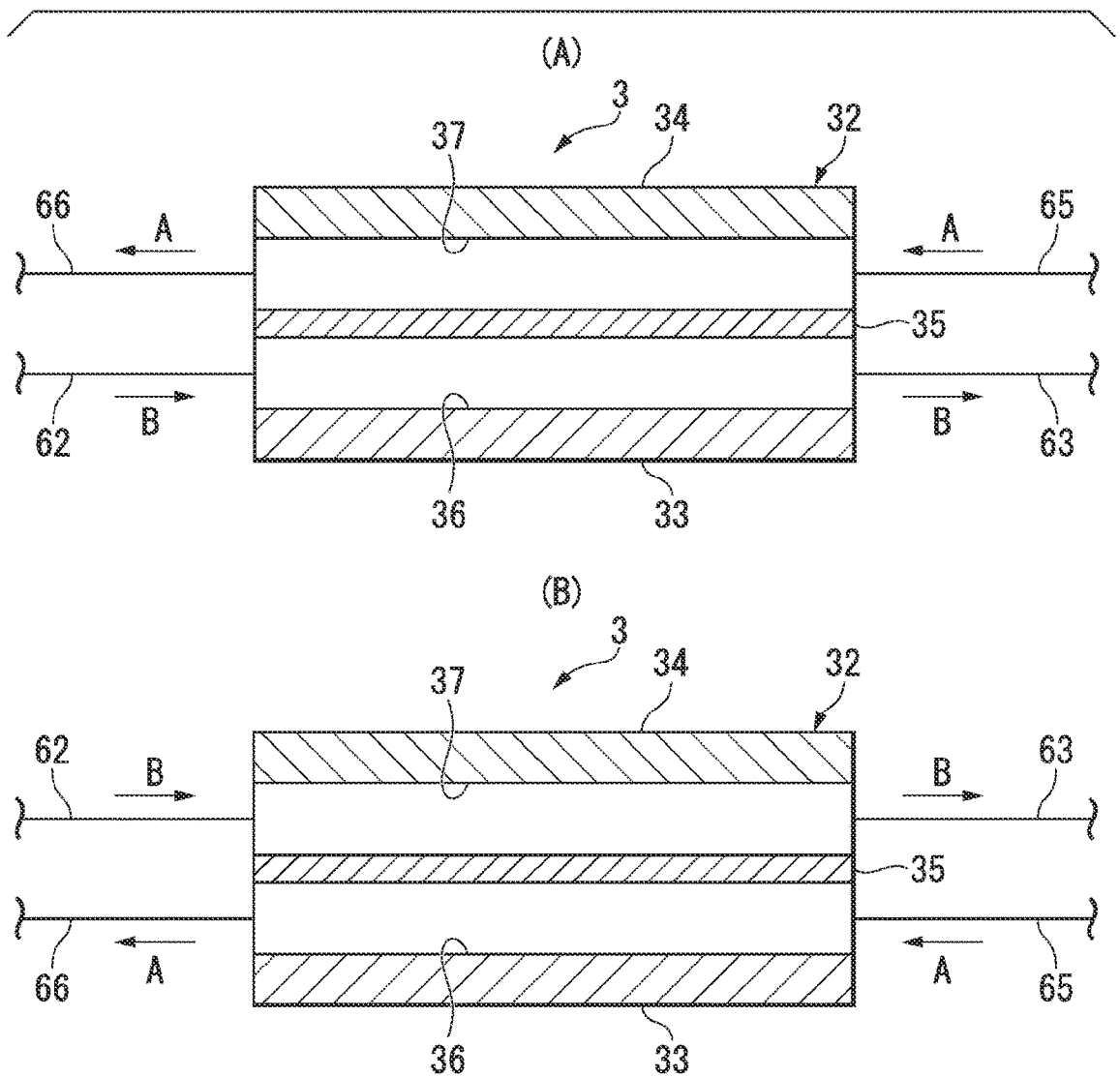
FIG. 3 is a schematic sectional view illustrating a nickel-hydride battery which is an example of a storage unit.

As illustrated in FIG. 3A, the storage unit 32 is a nickel-hydride battery including a positive electrode 33, a negative electrode 34, a separator 35 provided between the positive electrode 33 and the negative electrode 34, a positive electrode side flow path 36 formed between the positive electrode 33 and the separator 35, and a negative electrode side flow path 37 formed between the negative electrode 34 and the separator 35. The positive electrode side flow path 36 and the negative electrode side flow path 37 can be formed by using, for example, a liquid flow path structure similar to the liquid flow path 23a of the electrochemical reaction device 2.

Examples of the positive electrode 33 include an electrode coated with a positive electrode active material on the positive electrode side flow path 36 side of a positive electrode current collector.

The positive electrode current collector is not particularly limited, and examples thereof include nickel foil and nickel-plated metal foil.

The positive electrode active material is not particularly limited, and examples thereof include nickel hydroxide and nickel oxyhydroxide.

Examples of the negative electrode 34 include an electrode coated with a negative electrode active material on the negative electrode side flow path 37 side of the negative electrode current collector.

The negative electrode current collector is not particularly limited, and examples thereof include a nickel mesh.

The negative electrode active material is not particularly limited, and examples thereof include known hydrogen occlusion alloys.

The separator 35 is not particularly limited, and examples thereof include an ion exchange membrane.

The nickel-hydride battery of the storage unit 32 is a flow cell in which the electrolytic solution flows through each of the positive electrode side flow path 36 on the positive electrode 33 side of the separator 35 and the negative electrode side flow path 37 on the negative electrode 34 side of the separator 35. In the carbon dioxide treatment apparatus 100, the electrolytic solution B supplied from the absorption unit 12 through the liquid flow path 62 and the electrolytic solution A supplied from the electrochemical reaction device 2 through the liquid flow path 65 flow through each of the positive electrode side flow path 36 and the negative electrode side flow path 37. Further, the connection of the liquid flow paths 62 and 63 to the storage unit 32 can be switched between being connected to the positive electrode side flow path 36 and being connected to the negative electrode side flow path 37, respectively. Similarly, the connection of the liquid flow paths 65 and 66 to the storage unit 32 can be switched between being connected to the positive electrode side flow path 36 and being connected to the negative electrode side flow path 37, respectively.

When the nickel-hydride battery is discharged, hydroxide ions are generated from water molecules at the positive electrode, and the hydroxide ions that has moved to the negative electrode receive hydrogen ions from the hydrogen occlusion alloy to generate water molecules. Therefore, from the viewpoint of discharge efficiency, it is advantageous that the electrolytic solution flowing through the positive electrode side flow path 36 is in a weak alkaline state, and it is advantageous that the electrolytic solution flowing through the negative electrode side flow path 37 is in a strong alkaline state. Therefore, at the time of discharge, as illustrated in FIG. 3A, it is preferable that the liquid flow paths 62 and 63 be connected to the positive electrode side flow path 36, the liquid flow paths 65 and 66 be connected to the negative electrode side flow path 37, the electrolytic solution B (weak alkali) supplied from the absorption unit 12 flow through the positive electrode side flow path 36, and the electrolytic solution A (strong alkali) supplied from the electrochemical reaction device 2 flow through the negative electrode side flow path 37. In other words, at the time of discharge, it is preferable that the electrolytic solution be circulated in the order of the absorption unit 12, the positive electrode side flow path 36 of the storage unit 32, the electrochemical reaction device 2, the negative electrode side flow path 37 of the storage unit 32, and the absorption unit 12.

Further, when a nickel-hydride battery is charged, water molecules are generated from hydroxide ions at the positive electrode, water molecules are decomposed into hydrogen atoms and hydroxide ions at the negative electrode, and hydrogen atoms are stored in a hydrogen occlusion alloy. Therefore, from the viewpoint of charge efficiency, it is advantageous that the electrolytic solution flowing through the positive electrode side flow path 36 is in a strong alkaline state, and it is advantageous that the electrolytic solution flowing through the negative electrode side flow path 37 is in a weak alkaline state. Therefore, at the time of charging, as illustrated in FIG. 3B, it is preferable that the liquid flow paths 62 and 63 be connected to the negative electrode side flow path 37, the liquid flow paths 65 and 66 be connected to the positive electrode side flow path 36, the electrolytic solution B (weak alkali) supplied from the absorption unit 12 flow through the negative electrode side flow path 37, and the electrolytic solution A (strong alkali) supplied from the electrochemical reaction device 2 flow through the positive electrode side flow path 36. In other words, at the time of charging, it is preferable that the electrolytic solution be circulated in the order of the absorption unit 12, the negative electrode side flow path 37 of the storage unit 32, the electrochemical reaction device 2, the positive electrode side flow path 36 of the storage unit 32, and the absorption unit 12.

In general, when a secondary battery is incorporated in an apparatus, the overall energy efficiency tends to decrease as much as the amount of charge/discharge efficiency. However, as described above, by using the pH gradients of the electrolytic solution A and the electrolytic solution B before and after the electrochemical reaction device 2, and by properly exchanging the electrolytic solutions flowing through the positive electrode side flow path 36 and the negative electrode side flow path 37 of the storage unit 32, it is possible to improve the charge/discharge efficiency of the "concentration overvoltage" of the electrode reaction represented by the Nernst equation.

The homologation reaction device 4 is a device for increasing the number of carbons by multimerizing ethylene generated by reducing carbon dioxide in the electrochemical reaction device 2.

Ethylene gas C generated by the reduction at the cathode 21 of the electrochemical reaction device 2 is fed to the reactor 41 through the gas flow path 67. In the reactor 41, the multimerization reaction of ethylene is carried out in the presence of an olefin multimerization catalyst. Accordingly, for example, it is possible to produce olefins having an extended carbon chain such as 1-butene, 1-hexene, and 1-octene.

The olefin multimerization catalyst is not particularly limited, and a known catalyst used for the multimerization reaction can be used. Examples thereof include a solid acid catalyst using silica alumina or zeolite as a carrier and a transition metal complex compound.

In the homologation reaction device 4 of this example, generated gas D after the multimerization reaction flowing out of the reactor 41 is fed to the gas-liquid separator 42 through the gas flow path 68. An olefin having 6 or more carbon atoms is a liquid at room temperature. Therefore, for example, in a case where an olefin having 6 or more carbon atoms is used as a target carbon compound, the temperature of the gas-liquid separator 42 is set to approximately 30° C. to make it possible to easily separate an olefin having 6 or more carbon atoms (olefin liquid E1) and an olefin having less than 6 carbon atoms (olefin gas E2). Further, by raising the temperature of the gas-liquid separator 42, the carbon number of the obtained olefin liquid E1 can be increased.

When the gas G1 supplied to the concentration unit 11 of the capturing device 1 is the atmosphere, the separated gas G3 fed from the concentration unit 11 through the gas flow path 71 may be used for cooling the generated gas D in the gas-liquid separator 42. For example, using the gas-liquid separator 42 equipped with a cooling pipe, the separated gas G3 is passed through the cooling pipe, the generated gas D is passed to the outside of the cooling pipe, and the gas is aggregated on the surface of the cooling pipe to obtain the olefin liquid E1. Further, since the olefin gas E2 separated by the gas-liquid separator 42 contains unreacted components such as ethylene and an olefin having a smaller number of carbon atoms than that of the target olefin, the olefin gas E2 is returned to the reactor 41 through the gas flow path 70 and can be reused for the multimerization reaction.

The multimerization reaction of ethylene in the reactor 41 is an exothermic reaction in which the feeder has a higher enthalpy than that of the product and the reaction enthalpy is negative. In the carbon dioxide treatment apparatus 100, a heat medium F is heated by using the reaction heat generated in the reactor 41 of the homologation reaction device 4, and the heat medium F is circulated to the heat exchanger 5 through the circulation flow path 69 to cause heat exchange between the heat medium F and the electrolytic solution B in the heat exchanger 5. Accordingly, the electrolytic solution B supplied to the electrochemical reaction device 2 is heated. In the electrolytic solution B using a strong alkaline aqueous solution, the dissolved carbon dioxide is difficult to separate as a gas even when the temperature is raised, and the reaction speed of redox in the electrochemical reaction device 2 is improved by raising the temperature of the electrolytic solution B.

The homologation reaction device 4 may further have a reactor that performs a hydrogenation reaction of an olefin obtained by multimerizing ethylene using hydrogen generated by the electrochemical reaction device 2, or a reactor that performs an isomerization reaction of an olefin or paraffin.

[Carbon Dioxide Treatment Method]

A carbon dioxide treatment method according to an aspect of the present invention is a method including the following steps (a) and (b). The carbon dioxide treatment method of the present invention can be used as a method of producing carbon compounds. In other words, by using the carbon dioxide treatment method of the present invention, a carbon compound obtained by reducing carbon dioxide or a carbon compound obtained by using a carbon compound obtained by reducing carbon dioxide as a raw material can be produced.

Step (a): Carbon dioxide gas is brought into contact with an electrolytic solution composed of a strong alkaline aqueous solution, and carbon dioxide dissolves in the electrolytic solution and absorbed.

Step (b): The dissolved carbon dioxide in the electrolytic solution is electrochemically reduced to generate carbon compounds and hydrogen.

Similar to the carbon dioxide treatment apparatus 100, in a case where the carbon dioxide treatment apparatus including a homologation reaction device is used, the carbon dioxide treatment method includes the following step (c) in addition to the steps (a) and (b). Hereinafter, as an example of the carbon dioxide treatment method, a case where the above-described carbon dioxide treatment apparatus 100 is used will be described.

Step (c): Ethylene generated by the reduction of dissolved carbon dioxide is multimerized.

In the carbon dioxide treatment method using the carbon dioxide treatment apparatus 100, first, exhaust gas, the atmosphere, and the like are supplied to the concentration unit 11 as gas G1 and the carbon dioxide is concentrated to obtain the concentrated gas G2. As described above, since the absorption of carbon dioxide in the electrolytic solution A in the absorption unit 12 assists the concentration, it is not necessary to concentrate the carbon dioxide to a high concentration in the concentration unit 11. The carbon dioxide concentration of the concentrated gas G2 can be appropriately set, and can be, for example, 25 to 85% by volume.

In the step (a), the concentrated gas G2 is supplied from the concentration unit 11 to the absorption unit 12, the concentrated gas G2 is brought into contact with the electrolytic solution A, and the carbon dioxide in the concentrated gas G2 dissolves in the electrolytic solution A and absorbed. The electrolytic solution B in which carbon dioxide dissolves is in a weak alkaline state. Further, the electrolytic solution B is supplied from the absorption unit 12 to the heat exchanger 5 via the storage unit 32, and the electrolytic solution B heated by heat exchange with the heat medium F is supplied to the electrochemical reaction device 2. The temperature of the electrolytic solution B supplied to the electrochemical reaction device 2 can be appropriately set, and can be, for example, 65 to 105° C.

In the step (b), the electrolytic solution B flows through the liquid flow path 23a of the electrochemical reaction device 2, power is supplied from the power storage device 3 to the electrochemical reaction device 2, and a voltage is applied between the cathode 21 and the anode 22. Then, at the cathode 21, the dissolved carbon dioxide in the electrolytic solution B is electrochemically reduced to produce a carbon compound, and water is reduced to generate hydrogen. At this time, at the anode 22, the hydroxide ions in the electrolytic solution B are oxidized to generate oxygen. The amount of dissolved carbon dioxide in the electrolytic solution B decreases as the reduction proceeds, and the electrolytic solution A in a strong alkaline state flows out of the outlet of the liquid flow path 23a. The gaseous carbon compound and hydrogen generated by the reduction permeate through the gas diffusion layer of the cathode 21, flow out of the electrochemical reaction device 2 through the gas flow path 24a, and are fed to the homologation reaction device 4.

In the step (c), the ethylene gas C generated by the reduction of carbon dioxide is fed to the reactor 41 and is brought into gas phase contact with the olefin multimerization catalyst in the reactor 41 to multimerize ethylene. Accordingly, an olefin in which ethylene is multimerized can be obtained. For example, in a case where an olefin having 6 or more carbon atoms is used as a target carbon compound, the generated gas D emitted from the reactor 41 is fed to the gas-liquid separator 42 and cooled to approximately 30° C. Then, the target olefin having 6 or more carbon atoms (for example, 1-hexene) is liquefied, and the olefin having less than 6 carbon atoms remains as a gas. Thus, it is possible to easily separate the olefin liquid E1 (target carbon compound) and the olefin gas E2. The carbon number of the olefin liquid E1 and the olefin gas E2 to be gas-liquid separated can be adjusted by the temperature of the gas-liquid separation.

The olefin gas E2 after gas-liquid separation can be returned to the reactor 41 and reused for the multimerization reaction. In this manner, in a case where an olefin having a smaller number of carbon atoms than that of the target olefin is circulated between the reactor 41 and the gas-liquid separator 42, it is preferable that the reactor 41 adjust the contact time between a raw material gas (a mixed gas of the ethylene gas C and the olefin gas E2) and the catalyst to control the conditions under which each molecule causes an average of one multimerization reaction. Accordingly, an unintentional increase in the number of carbon atoms of the olefin generated in the reactor 41 is suppressed, and thus, the gas-liquid separator 42 can selectively separate the olefin having a desired number of carbon atoms (olefin liquid E1).

According to such a method, valuable resources can be efficiently obtained from a renewable carbon source with high selectivity. Therefore, it does not require a large-scale refining facility such as a distillation column required in conventional petrochemistry using the Fischer-Tropsch (FT) synthesis method or the MtG method, and is economically advantageous overall.

The reaction temperature of the multimerization reaction is preferably 200 to 350° C.

Regarding the reaction time of the multimerization reaction, that is, the contact time between the raw material gas and the olefin multimerization catalyst, 10 to 250 g·min/mol is preferable from the viewpoint that the excessive multimerization reaction is suppressed and the selectivity of the target carbon compound is improved.

Figure 4:
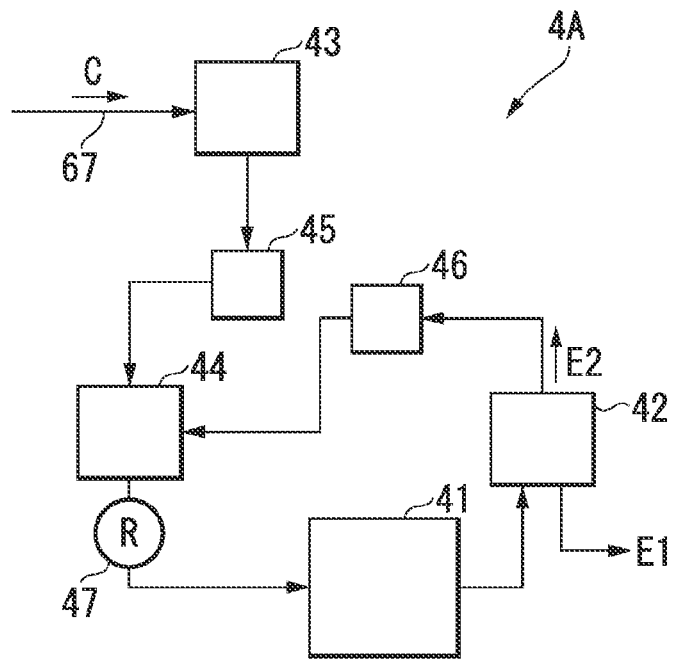
FIG. 4 is a block diagram illustrating an example of a homologation reaction device.

In a case where an olefin having a smaller number of carbon atoms than that of the target olefin is circulated between the reactor 41 and the gas-liquid separator 42 and the contact time between the raw material gas and the catalyst is adjusted to improve the selectivity of the carbon compound to be produced, for example, a homologation reaction device 4A of the aspect illustrated in FIG. 4 may be used. The same parts as those of the homologation reaction device 4 of FIG. 1 in FIG. 4 are given the same reference numerals, and the description thereof will be omitted.

In addition to the reactor 41 and the gas-liquid separator 42, the homologation reaction device 4A further includes a tank 43, a tank 44, a compressor 45, a compressor 46, and a pressure reducing valve 47. The tank 43 stores the ethylene gas C generated by the electrochemical reaction device 2. The tank 44 stores the ethylene gas C supplied from the tank 43 and the olefin gas E2 supplied from the gas-liquid separator 42. The compressor 45 compresses the ethylene gas C supplied from the tank 43 to the tank 44. The compressor 46 compresses the olefin gas E2 supplied from the gas-liquid separator 42 to the tank 44. The pressure reducing valve 47 is provided in the gas flow path connecting the tank 44 and the reactor 41. Measuring equipment such as a pressure gauge can be appropriately installed in the gas flow path connecting the tank 43 and the compressor 45, the gas flow path connecting the compressor 45 and the tank 44, and the like.

In the homologation reaction device 4A, the time for the mixed gas of the ethylene gas C and the olefin gas E2 to come into contact with the catalyst in the reactor 41 can be adjusted by compression by the compressors 45 and 46 and the adjustment of the pressure reducing valve 47. 1-hexene can be obtained as the olefin liquid E1 by using the homologation reaction device 4A, for example, by setting the temperature of the gas-liquid separator 42 to approximately 30° C. and circulating an olefin having less than 6 carbon atoms as the olefin gas E2.

Figure 5:
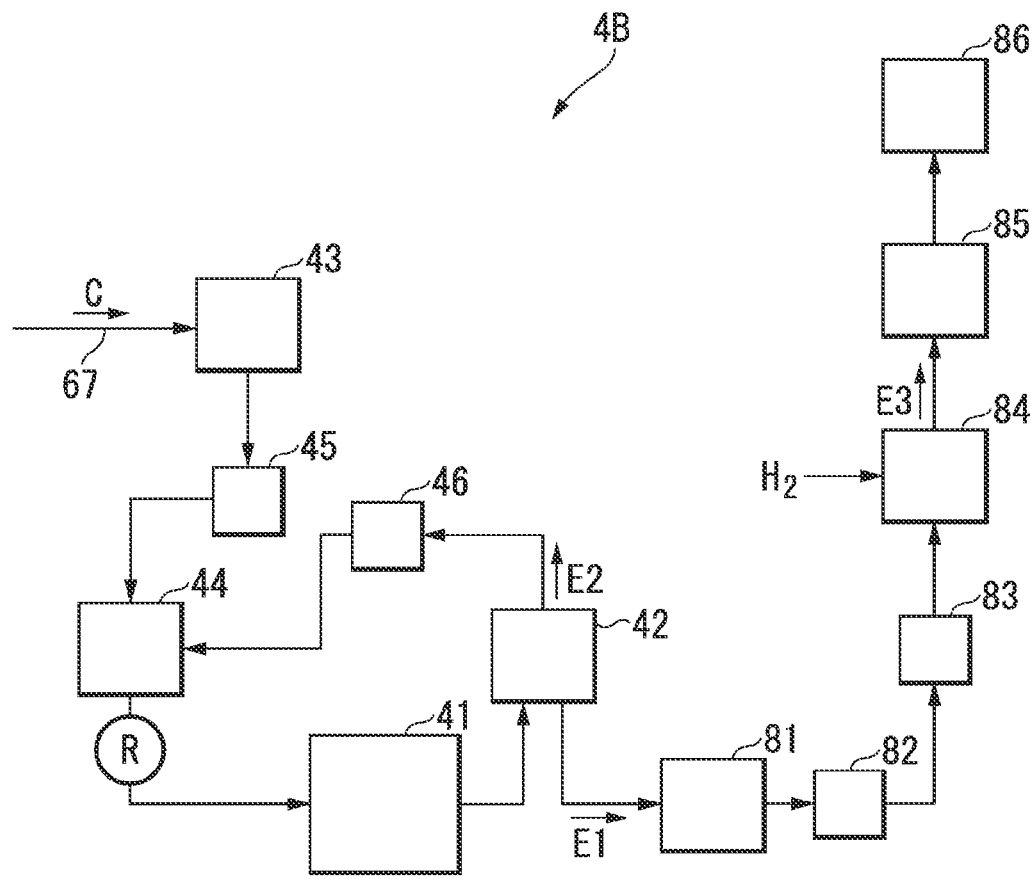
FIG. 5 is a block diagram illustrating an example of the homologation reaction device.

Furthermore, in a case of hydrogenating the olefin obtained by multimerizing ethylene to obtain paraffin, or in a case of further isomerizing, for example, a homologation reaction device 4B of the aspect illustrated in FIG. 5 may be used. The same parts as those of the homologation reaction device 4A of FIG. 4 in FIG. 5 are given the same reference numerals, and the description thereof will be omitted.

The homologation reaction device 4B is the same configuration as the homologation reaction device 4A except that a tank 81, a vaporizer 82, a compressor 83, a reactor 84, a heat exchanger 85, and a tank 86 are provided in this order downstream of the gas-liquid separator 42 on the side where the olefin liquid E1 is taken out. The reactor 84 is a reactor that performs a hydrogenation reaction and an isomerization reaction of an olefin. Liquid feeding means such as a pump can be appropriately installed in the liquid flow path connecting the tank 81 and the vaporizer 82 and in the liquid flow path connecting the heat exchanger 85 and the tank 86. Measuring equipment such as a pressure gauge can be appropriately installed in the gas flow path connecting the compressor 83 and the reactor 84.

In a case of using the homologation reaction device 4B, for example, the olefin liquid E1 obtained by the gas-liquid separator 42 is temporarily stored in the tank 81, then vaporized by the vaporizer 82 and supplied to the reactor 84. Further, the hydrogen generated by the electrochemical reaction device 2 is supplied to the reactor 84 to hydrogenate the olefin and further isomerize the olefin. Next, the isomerized paraffin gas E3 after the reaction is cooled by the heat exchanger 85, liquefied, and accommodated in the tank 86. For example, in a case where 1-hexene is obtained as the olefin liquid E1 from the gas-liquid separator 42, the hydrogenation reaction and the isomerization reaction can be carried out in the reactor 84 to obtain i-hexane.

As the hydrogenation reaction of the olefin, a known method can be adopted, and examples thereof include a method of hydrogenation reaction using a solid acid catalyst such as silica alumina or zeolite.

As the isomerization reaction, a known method can be adopted, and examples thereof include a method of isomerization reaction using a solid acid catalyst such as silica alumina or zeolite.

The reaction temperature of the reactor 84 is preferably 200 to 350° C.

As described above, in one aspect of the present invention, an electrolytic solution composed of a strong alkaline aqueous solution is used, and an electrolytic solution in which carbon dioxide has dissolved by a capturing device is supplied between the cathode and the anode, and the dissolved carbon dioxide in the electrolytic solution is electrochemically reduced. Therefore, the energy efficiency of carbon dioxide capture and reduction is high, and the carbon dioxide loss is also reduced.

In addition, the present invention is not limited to the above-described aspect.

Figure 6:
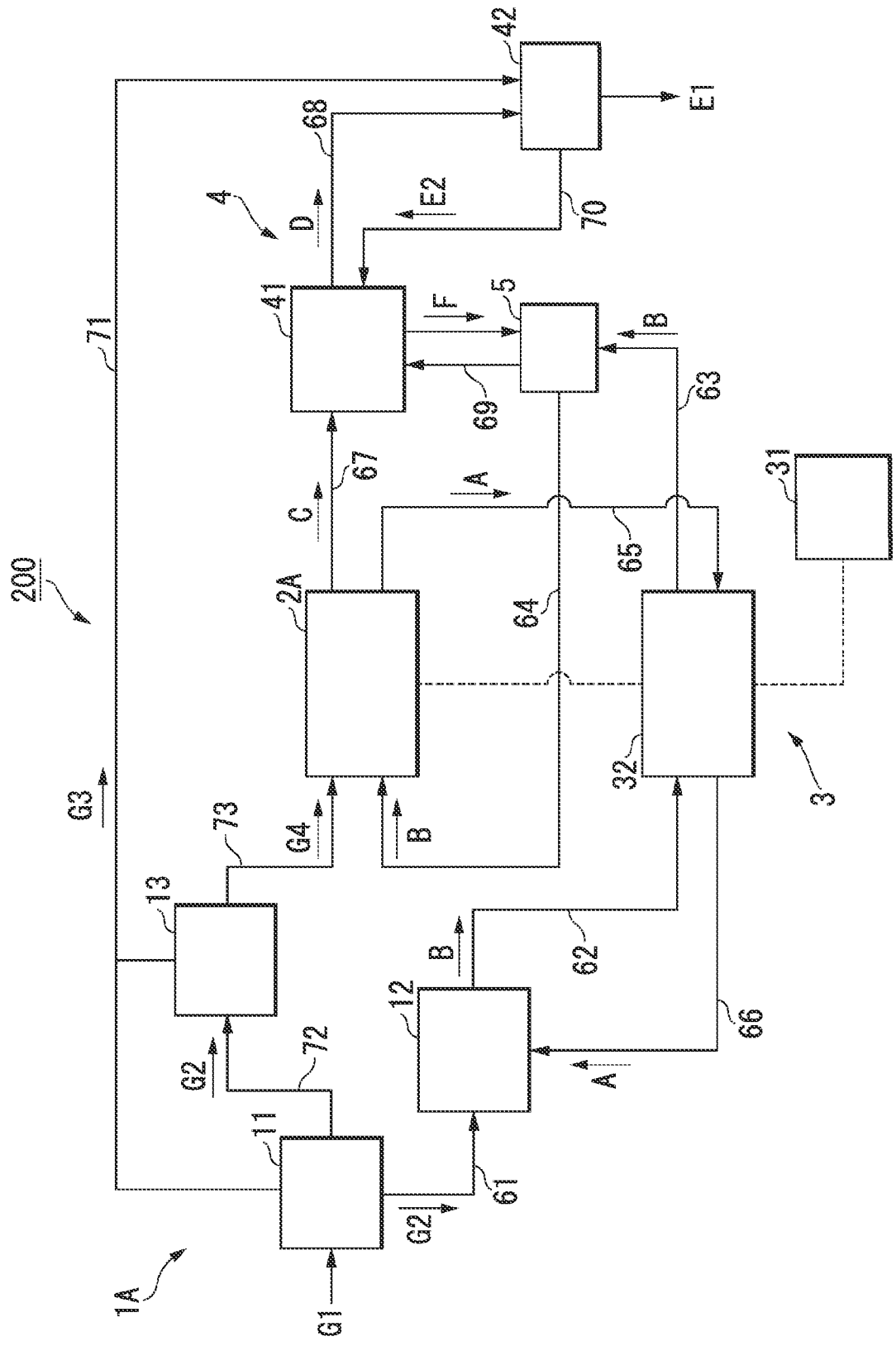
FIG. 6 is a block diagram illustrating a carbon dioxide treatment apparatus according to another embodiment.

For example, the present invention may be related to a carbon dioxide treatment apparatus in which carbon dioxide gas is further supplied from the concentration unit of the capturing device to the side of the cathode opposite to the anode in the electrochemical reaction device. Specifically, for example, a carbon dioxide treatment apparatus 200 illustrated in FIG. 6 may be used. The same parts as those in FIG. 1 in FIG. 6 are given the same reference numerals, and the description thereof will be omitted. The carbon dioxide treatment apparatus 200 has the same configuration as the carbon dioxide treatment apparatus 100 except that a capturing device 1A is provided instead of the capturing device 1 and an electrochemical reaction device 2A is provided instead of the electrochemical reaction device 2.

The capturing device 1A has the same configuration as the capturing device 1 except for the configuration described below. The capturing device 1A further includes the concentration unit 13 in addition to the concentration unit 11 and the absorption unit 12. The concentration unit 11 and the concentration unit 13 are connected by a gas flow path 72. The concentration unit 13 and the electrochemical reaction device 2A are connected by a gas flow path 73. The concentrated gas G2 in which carbon dioxide has been concentrated in the concentration unit 11 is supplied to each of the absorption unit 12 and the concentration unit 13, and the carbon dioxide is further concentrated in the concentration unit 13. The concentration unit 13 is not particularly limited, and the same as those exemplified in the concentration unit 11 can be exemplified, and chemical adsorption, particularly temperature swing adsorption, is preferable.

Figure 7:
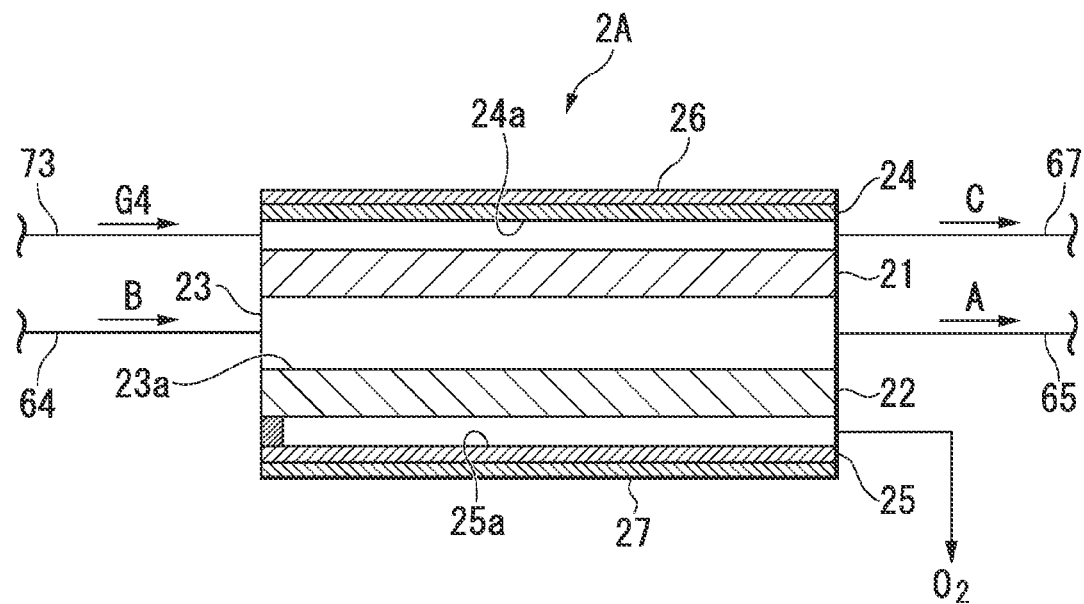
FIG. 7 is a schematic sectional view illustrating an example of the electrolytic cell of the electrochemical reaction device.

As illustrated in FIG. 7, the electrochemical reaction device 2A has the same configuration as the electrochemical reaction device 2 except that concentrated gas G4 in which the carbon dioxide of the concentrated gas G2 is further concentrated in the concentration unit 13 passes through the gas flow path 73 and is supplied to the gas flow path 24a on the side of the cathode 21 opposite to the anode 22. In the electrochemical reaction device 2A, the dissolved carbon dioxide in the electrolytic solution B is supplied between the cathode 21 and the anode 22, and carbon dioxide gas is further supplied from the side of the cathode 21 opposite to the anode 22.

In the carbon dioxide treatment method using the carbon dioxide treatment apparatus 200, while the dissolved carbon dioxide in the electrolytic solution B supplied between the cathode 21 and the anode 22 is electrochemically reduced, the carbon dioxide gas supplied to the side of the cathode 21 opposite to the anode 22 is electrochemically reduced. Accordingly, the efficiency of supplying carbon dioxide to the cathode 21 becomes higher than that in a case of only supplying carbon dioxide by the electrolytic solution, and the current density at the time of electrolysis becomes higher, and thus, the efficiency of carbon dioxide reduction is further improved.

In a case where carbon dioxide gas is supplied to the electrochemical reaction device 2A, there is no concentration assist due to the absorption of carbon dioxide to the electrolytic solution A, and thus, the carbon dioxide of the concentrated gas G2 obtained in the concentration unit 11 is further concentrated in the concentration unit 13 to obtain the concentrated gas G4. However, since the supply of carbon dioxide to the electrochemical reaction device 2A is a combination of the supply as dissolved carbon dioxide using the electrolytic solution and the supply as gas, the carbon dioxide supply amount increases as becoming closer to the electrode compared to a case where only gas is supplied, and the loss also decreases. The carbon dioxide concentration of the concentrated gas G4 can be appropriately set, and can be, for example, 80 to 100% by volume.

Figure 8:
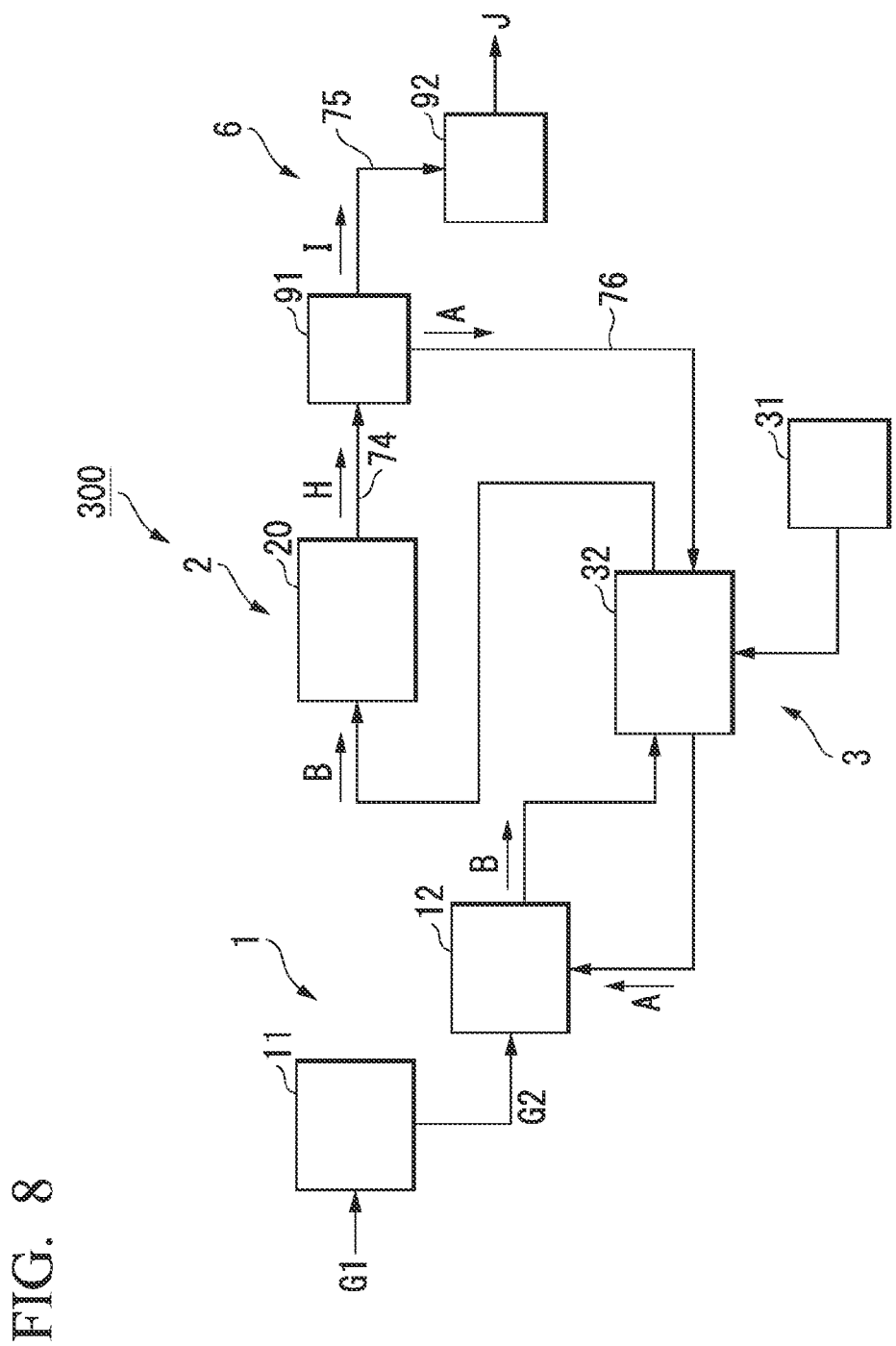
FIG. 8 is a block diagram illustrating a carbon dioxide treatment apparatus according to another embodiment.

The carbon dioxide treatment apparatus may further include an ethanol purification device for purifying ethanol generated by reducing carbon dioxide in the electrochemical reaction device. Specifically, for example, a carbon dioxide treatment apparatus 300 illustrated in FIG. 8 may be used. The same parts as those in FIG. 1 in FIG. 8 are given the same reference numerals, and the description thereof will be omitted.

The carbon dioxide treatment apparatus 300 includes an ethanol purification device 6 instead of the homologation reaction device 4 and the heat exchanger 5 in the carbon dioxide treatment apparatus 100.

The ethanol purification device 6 includes a distillation column 91 and a gas-liquid separator 92. The distillation column 91 is connected to the liquid flow path 23a of the electrochemical reaction device 2 by the liquid flow path 74. The distillation column 91 and the gas-liquid separator 92 are connected by a gas flow path 75. The distillation column 91 and the storage unit 32 are connected by a liquid flow path 76. Similar to the liquid flow path 65 in the carbon dioxide treatment apparatus 100, the connection of the liquid flow path 76 to the storage unit 32 is switched between being connected to the positive electrode side flow path 36 and being connected to the negative electrode side flow path 37.

In the carbon dioxide treatment apparatus 300, ethanol generated by reducing carbon dioxide at the cathode 21 is fed to the distillation column 91 through the liquid flow path 74 as a mixed liquid H with the electrolytic solution A and distilled. Ethanol gas I separated by distillation is fed to the gas-liquid separator 92 through the gas flow path 75 and captured as liquid ethanol J. The electrolytic solution A from which ethanol is separated in the distillation column 91 is fed to the storage unit 32 through the liquid flow path 76. The electrolytic solution fed to the storage unit 32 is flowed through the negative electrode side flow path 37 during discharge and is flowed through the positive electrode side flow path 36 at the time of charging.

In the carbon dioxide treatment method using the carbon dioxide treatment apparatus 300, as in the method using the carbon dioxide treatment apparatus 100, carbon dioxide dissolves in the electrolytic solution B and supplied to the electrochemical reaction device 2 as dissolved carbon dioxide. Then, ethanol generated by reducing the dissolved carbon dioxide in the electrochemical reaction device 2 is purified by the ethanol purification device 6 to obtain ethanol (step (d)). In this manner, ethanol can be produced by utilizing the carbon dioxide treatment method.

Further, the carbon dioxide treatment apparatus provided with the ethanol purification device may have an aspect including the ethanol purification device 6 instead of the homologation reaction device 4 and the heat exchanger 5 in the carbon dioxide treatment apparatus 200. Further, the present invention may be related to a carbon dioxide treatment apparatus provided with the ethanol purification device 6 in addition to the homologation reaction device 4 and the heat exchanger 5.

Further, the carbon dioxide treatment apparatus of the embodiment may be a carbon dioxide treatment apparatus that does not include all of the homologation reaction device, the heat exchanger, and the ethanol purification device. For example, ethylene may be produced by using a carbon dioxide treatment method using this carbon dioxide treatment apparatus.

Further, in the carbon dioxide treatment apparatus of the embodiment, the electrochemical reaction device and the power storage device do not share the electrolytic solution, and the electrolytic solution may be circulated only between the absorption unit of the capturing device and the electrochemical reaction device.

In addition, it is appropriately possible to replace the configuration elements in the above-described embodiments with well-known configuration elements without departing from the spirit of the present invention, and the above-described modification examples may be appropriately combined.

EXPLANATION OF REFERENCES 100, 200, 300 Carbon dioxide treatment apparatus
1, 1A Capturing device
2, 2A Electrochemical reaction device
3 Power storage device
4, 4A, 4B Homologation reaction device
5 Heat exchanger
6 Ethanol purification device
11 Concentration unit
12 Absorption unit
21 Cathode
22 Anode
23a Liquid flow path
31 Conversion unit
32 Storage unit
33 Positive electrode
34 Negative electrode
35 Separator
36 Positive electrode side flow path
37 Negative electrode side flow path
41 Reactor
42 Gas-liquid separator
91 Distillation column
92 Gas-liquid separator
A, B Electrolytic solution

What is claimed is:

1. A carbon dioxide treatment apparatus comprising:
a capturing device that captures carbon dioxide;
an electrochemical reaction device that electrochemically reduces carbon dioxide; and
a power storage device that supplies power to the electrochemical reaction device, wherein
the capturing device includes an absorption unit that brings an electrolytic solution composed of a strong alkaline aqueous solution and carbon dioxide gas into contact with each other to dissolve carbon dioxide in the electrolytic solution and absorb the carbon dioxide, the electrochemical reaction device includes a cathode, an anode, and a liquid flow path provided between the cathode and the anode through which the electrolytic solution that has absorbed carbon dioxide in the absorption unit flows, and reduces the dissolved carbon dioxide in the electrolytic solution at the cathode, the power storage device includes a conversion unit that converts renewable energy into electric energy, and a storage unit that stores the electric energy converted by the conversion unit, and the electrolytic solution is circulated and shared between the absorption unit, the storage unit, and the electrochemical reaction device.

2. The carbon dioxide treatment apparatus according to claim 1, wherein the storage unit is a nickel-hydride battery, the nickel-hydride battery has a positive electrode, a negative electrode, a separator provided between the positive electrode and the negative electrode, a positive electrode side flow path provided between the positive electrode and the separator, and a negative electrode side flow path provided between the negative electrode and the separator, when the nickel-hydride battery is discharged, the electrolytic solution is circulated in an order of the absorption unit, the positive electrode side flow path, the electrochemical reaction device, the negative electrode side flow path, and the absorption unit, and when the nickel-hydride battery is charged, the electrolytic solution is circulated in an order of the absorption unit, the negative electrode side flow path, the electrochemical reaction device, the positive electrode side flow path, and the absorption unit.

3. The carbon dioxide treatment apparatus according to claim 1, wherein the capturing device further has a concentration unit that concentrates carbon dioxide, and carbon dioxide gas is supplied from the concentration unit to a side of the cathode opposite to the anode.

4. The carbon dioxide treatment apparatus according to claim 1, further comprising:

a homologation reaction device that increases the number of carbons by multimerizing ethylene generated by reducing carbon dioxide in the electrochemical reaction device.

5. The carbon dioxide treatment apparatus according to claim 4, further comprising:

a heat exchanger that heats the electrolytic solution by exchanging heat between a heat medium heated by the heat generated by reaction in the homologation reaction device and the electrolytic solution.

6. The carbon dioxide treatment apparatus according to claim 1, further comprising:

an ethanol purification device that purifies ethanol generated by reducing carbon dioxide by the electrochemical reaction device.

* * * * *